United States Patent [19]
Haar et al.

[11] Patent Number: 4,838,999
[45] Date of Patent: Jun. 13, 1989

[54] METHOD FOR THE ELECTROCHEMICAL ANALYSIS OF ELECTROLYTIC COMPONENTS IN A SAMPLE LIQUID

[75] Inventors: Hans-Peter Haar, Weilheim; Hermann Edelmann, Tutzing; Horst Herrmann, Bernried; Joachim Thiery, Mannheim, all of Fed. Rep. of Germany

[73] Assignee: Boehringer Mannheim GmbH, Mannheim, Fed. Rep. of Germany

[21] Appl. No.: 233,329

[22] Filed: Aug. 17, 1988

Related U.S. Application Data

[63] Continuation of Ser. No. 591,780, Mar. 21, 1984, abandoned.

[30] Foreign Application Priority Data

Apr. 11, 1983 [DE] Fed. Rep. of Germany ....... 3312922

[51] Int. Cl.$^4$ .................. G01N 1/14; G01N 27/26
[52] U.S. Cl. .................... 204/1 T; 73/1 R; 204/409; 422/68; 422/82; 422/100
[58] Field of Search ............. 204/400, 409, 416, 435, 204/1 T; 422/63, 68, 100; 324/425, 438, 450; 73/1 R

[56] References Cited

U.S. PATENT DOCUMENTS

| | | | |
|---|---|---|---|
| 3,556,950 | 1/1971 | Dahms | 324/425 X |
| 3,657,095 | 4/1972 | Tosteson | 204/1 T X |
| 3,707,455 | 12/1972 | Derr et al. | 204/415 X |
| 3,846,257 | 11/1974 | Riseman et al. | 204/409 X |
| 4,318,884 | 3/1982 | Suzuki | 422/63 |
| 4,318,885 | 3/1982 | Suzuki et al. | 422/100 X |
| 4,342,464 | 8/1982 | Diamond et al. | 324/450 |

FOREIGN PATENT DOCUMENTS

2829783 1/1979 Fed. Rep. of Germany.
2851532 6/1980 Fed. Rep. of Germany.
3046016 9/1981 Fed. Rep. of Germany.

OTHER PUBLICATIONS

Lieberman et al., "Anodic Stripping Voltametry ... electrode", Analytical Chem., vol. 46, No. 1, pp. 20-23, 1/1974.

Primary Examiner—Nam X. Nguyen
Attorney, Agent, or Firm—Felfe & Lynch

[57] ABSTRACT

The present invention provides a device for the electrochemical analysis of electrolytic components in a sample liquid (58), especially of a body fluid, with a selective measurement electrode (20) for a kind of ion to be analysed, a reference half cell, which includes a conducting-off element (30) cooperating in the operational state with a reference electrolyte (56), and a voltage measurement device (34) for the measurement of the voltage between the measurement electrode and the conducting-off element (30), wherein the measurement electrode (20) is arranged on a pipe (22) provided with a sucking-in opening (23) for the sample liquid (58), the conducting-off element (30) of the reference half cell being arranged on the pipe (22) in such a manner that it directly contacts a liquid (56) present therein, the conducting-off element (30) thereby being arranged in the pipe (22) in the sucking-in direction behind the measurement electrode (20), a sucking-in device (36) being provided through which a sample liquid (58) can be sucked in and, together with a liquid reference electrolyte present in the pipe (22) or previously sucked in, is transportable subsequent to this in the same direction in the pipe (22) and the voltage measurement device (34) is activatable in a measurement operational state in that the sample liquid (58) contacts the measurement electrode and the reference liquid (56) contacts the conducting-off element (30) and both liquids are in contact with one another, making possible an ion exchange.

10 Claims, 7 Drawing Sheets

METHOD FOR THE ELECTROCHEMICAL ANALYSIS OF ELECTROLYTIC COMPONENTS IN A SAMPLE LIQUID

This application is a continuation of Ser. No. 591,780, filed 3-21-84, now abandoned.

The present invention is concerned with an apparatus for the electrochemical analysis of electrolytic components of a sample liquid, especially of a body fluid, with a selective measurement electrode for a type of ion to be analysed, a reference half cell, which includes a conducting-off element cooperating with a reference electrolyte in the operative state, and a voltage measurement device for the measurement of the voltage between the measurement electrode and the conducting-off element.

In recent years, electrolyte analysers have achieved increasing importance, especially in the analysis of electrolytic components of body fluids.

In particular, the concentration of potassium or sodium in blood or urine can be quickly and simply determined with the help of an electrochemical measurement cell and provides valuable diagnostic information.

Electrochemical measurement cells always have two electrodes, namely, the actual measurement electrode and the comparison or reference electrode. The actual measurement electrode can be constructed in different ways. In clicical chemistry, ion-selective electrodes are especially usual which, as a rule, have an ion-sensitive membrane, a conducting-off electrolyte and a conducting-off element. Instead of the membrane, solid body electrolytes, for example selectively-conducting glasses or ceramic materials, are also used. The construction of the measurement electrodes is not the subject matter of the present invention so that it is not necessary to discuss this here in more detail. On the contrary, for the present invention, in principle there can be used all known measurement electrodes.

The measurement electrode is brought into contact with the sample liquid in order to determine the concentration of the ions in the electrolytes to be analysed. As mentioned, for this purpose, the voltage between the measurement electrode (i.e. its conducting-off element) and a reference electrode is determined, the reference electrode also being in contact with the measurement liquid. In order to achieve a reproducible measurement, the reference electrode must always provide the same reference potential, independently of the sample liquid. For this purpose, it is necessary that the reference electrode includes an electrolyte which has a constant activity of a particular type of ion. This reference electrolyte is in contact with the conducting-off element, a reversible electrode reaction, which provides the constant reference potential, thereby taking place at the point of contact.

There are many constructions for reference electrodes. In especially favourable cases, it is possible to use the measurement liquid itself as reference electrolyte because, ab initio, this contains a type of ion for which a corresponding conducting-off element is available or because it is possible to mix the sample liquid with a corresponding electrolyte solution without otherwise disturbing the measurement. In this manner, there is obtained a so-called "measurement chain without transfer".

However, in the case of the analysis of human body fluids, it is, as a rule, not possible to use such measurement chains without transfer. This applies especially when it is desired directly to determine the electrolyte concentration of urine or blood without any kind of previous preparation steps. In this case, only reference eledtrodes with transfer can be used, i.e. reference electrodes which have their own reference electrolyte differing in composition from the measurement liquid. From this follows directly the problem that an electrolyte bridge must be present between the measurement solution and the reference electrolyte which, on the one hand, makes possible the necessary ion conduction (diffusion) and, on the other hand, prevents as far as possible the mutual mixing of the two liquids with one another. This contact zone between the reference electrolyte and the measurement liquid is the most common cause of problems and disturbances in the use of electrochemical measurement cells in clinical chemistry. As separating elements for preventing the exchange between the two liquids, there have been suggested various forms of frits, stoppers and other porous constructional elements which, however, all have a very strong tendency to become blocked up and are difficult to clean. Therefore, in clinical chemistry, ground connections have proved to be especially useful, in the case of which non-greased ground glass connections form the separating element, the narrow gap between the ground parts, which is filled with electrolyte, thereby permitting a sufficient ion transport. However, a disadvantage of ground connections is their comparatively large consumption of electrolyte, the result of which is that these electrodes must be constantly refilled, and the comparatively great contamination of the measurement solution. Further details can be seen, for example, from the book by Karl Camman entitled "Das Arbeiten mit ionselectiven Elektroden", second edition, pub. Springer-Verlag, 1977.

In order, inter alia, to avoid the problems with the construction of the electrolyte bridge, in the case of some devices used in clinical chemistry, a flow-through process is employed. In this case, the measurement liquid is sucked in via a pipe on which is arranged an ion-selective measurement electrode. In the direction of flow behind the measurement electrode, a second pipe with a very samll opening opens into the sample liquid pipe. This pipe is filled with a salt bridge electrolyte which produces the ion-conductive connection to a reference electrode arranged on this pipe. In operation, a small amount of the salt bridge electrolyte continuously flow into the sample pipe and is sucked up with the sample liquid. It is thereby avoided that reference electrolyte liquid or the salt bridge electrolyte pass into the region of the measurement electrode or sample liquid into the region of the reference electrode because the mixture resulting in the point of discharge is constantly sucked off. However, such a flowthrough system is laborious to construct and has a comparatively high consumption of salt bridge electrolyte and sample liquid.

There are also greatly differing outer constructions of electrochemical measurement cells. Thus, Federal Republic of Germany Patent Specification No. 30 46 016 describes an electrolyte analyser on which the electrochemical measurement is to be combined with the possibility of transferring a liquid within a comparatively large analysis apparatus from one vessel to another. For this reason, the measurement electrode is, in this case, constructed as an ion-selective field effect transistor and is arranged on a pipe which simultaneously serves for sucking in the measurement liquid. The reference electrode is also arranged on the pipe and is constructed in a wholly conventional manner. The sucking-in device, which is necessary for the transfer of the liquid, simultaneously fulfills the task of sucking in the measurement liquid to such an extent that it is in contact not only with the measurement electrode but also with the reference electrode so that an electrochemical measurement is possible.

It is an object of the present invention to provide an electrochemical electrolyte analyser which substantially avoids the problems described above which are involved with the electrolyte bridges, is thereby simple in construction and inexpensive to produce and with which a high degree of dependability can be achieved. Thus, according to the present invention, there is provided a device for the electrochemical analysis of electrolytic components in a sample liquid, especially of a body fluid, with a selective measurement electrode for a kind of ion to be analysed, a reference half cell, which includes a conducting-off element co-operating in the operational state with a reference electrolyte, and a voltage measurement device for the measurement of the voltage between the measurement electrode and the conducting-off element, wherein the measurement electrode is arranged on a pipe provided with a sucking-in opening for the sample liquid, the conducting-off element of the reference half cell being arranged on the pipe in such a manner that it directly contacts a liquid present therein, the conducting-off element thereby being arranged in the pipe in the sucking-in direction behind the measurement electrode, a sucking-in device being provided through which a sample liquid can be sucked in and, together with a liquid reference electrolyte present in the pipe or previously sucked in, is transportable subsequent to this in the same direction in the pipe and the voltage measurement device is activatable in a measurement operational state in that the sample liquid contacts the measurement electrode and the reference liquid contacts the conducting-off elements and both liquids are in contact with one another, making possible an ion exchange.

Whereas in the case of the device described in Federal Republic of Germany Patent Specification No. 30 46 016, the reference electrode is, in its totality, arranged on the pipe and is there contacted by the measurement liquid, i.e. must have a electrolyte bridge at the point of contact, on the side of which remote from the pipe there is present the reference electrolyte and a corresponding conducting-off element, in the case of the construction according to the present invention, the conducting-off element itself projects into the pipe. Before sucking in the measurement solution, the pipe is filled at least in its lower part, i.e. in the neighbourhood of the sucking-in opening, with the reference electrolyte liquid. If, now, the sample liquid is sucked in, then, subsequent to the reference electrolyte, it is transported in the pipe like this and in the same direction. Since, according to the present invention, the conducting-off element is arranged in the sucking-in direction behind the measurement electrode, the contact zone between both liquids first reaches the measurement electrode and, in the case of further transport of the liquids, a state is reached in which the sample liquid contacts the measurement electrode and the reference liquid contacts the conducting-off element, while both liquids are in diffusive contact with one another, making possible an ion exchange. This operational state of the apparatus is called the measurement operational state. In this state, the voltage measurement device is activated, i.e. the voltage between the measurement electrode and the conducting-off element of the reference half cell is measured.

Especially preferably, a reference electrolyte is used which, at the same time, contains the type of ion to be determined in a known activity. Such a kind of reference electrolyte forms a combined reference/standard solution. If there is now measured the voltage in an operational state, in which the reference electrolyte solution simultaneously contacts not only the measurement electrode but also the conducting-off element of the reference half cell, then there is measured the voltage corresponding to the known activity of the type of ion to be determined, i.e. a calibration value is measured. Therefore, the corresponding operational state is also to be called the calibration operational state.

The use of a combined reference/standard solution is known from U.S. Pat. No. 4,342,964 in connection with a device for pH value determination but which otherwise is constructed in a different manner. In the present case, this preferred measure permits an especially simple handling. Thus, it is no longer necessary to carry out special calibration and standard measurements. On the contrary, the reference electrolyte, which simultaneously serves as standard, is simply sucked in, the calibration measurement is carried out and subsequently the sample is then sucked in until the measurement operational state is reached and the unknown activity of the type of ion to be determined can be measured in the measurement solution. More particularly, such measurements can be carried out in various ways, which will be discussed hereinafter in more detail.

The principle, the sucking-in procedure can take place continuously, whereby the measurement liquid must then be sucked in so slowly that the state defined as the measurement operational state is maintained for such a period of time as is needed for the voltage measurement. However, it is preferred to provide a stepwise operating sucking-in device in which the volume of a sucking-in step is so synchronised with the pipe volume that the measurement operational state is reached. In this way, more time is available for the electrochemical measurement and the constructional expense is reduced.

Since, in the most general embodimental form of the present invention, in the contact zone between the measurement liquid and the reference electrolyte, means are not provided for preventing the mutual mixing of these liquids, the sucking-in of the measurement liquid subsequent to the reference liquid and the subsequent measurement must take place relatively quickly. In order to increase the utilisable measurement time and therewith to make possible more accurate measurements, according to an especially preferred embodiment of the present invention, in the region of the pipe in which is present the contact zone between reference liquid and measurement liquid in the measurement operational state, i.e. when the voltage measurement device is activated, there is provided an electrolyte bridge which prevents the exchange between the reference electrolyte and the sample liquid and, at the same time, ensures a sufficient diffusive contact between both liquids. For the fulfilment of the initially-described requirements, such an electrolyte bridge can be constructed in various ways. In particular, there can be considered constrictions or capillary constructions in the corresponding region of the pipe, which result in a diminution of the cross-sectional area. In the case of the use of such an electrolyte bridge, there exists, however, not only the danger of stoppage explained hereinbefore in detail but also the cleaning problems there also mentioned. Furthermore, such an electrolyte bridge in the form of a capillary construction or constriction is, of necessity, arranged at a particular place on the pipe (namely, there where, in the measurement operational state, there is the contact zone between the two liquids). Consequently, it can then only prevent the exchange between reference electrolyte and sample liquid in the desired manner when the contact zone is present at this point of the pipe. Consequently, an electrolyte bridge construction is desirable in which the mixing up of the liquids is also prevented during their movement through the pipe.

For this purpose, there is especially preferred a novel electrolyte bridge between sample liquid and reference liquid which includes a gas bubble arranged between the liquids, which bubble is electrolytically bridged over by at least one liquid connection maintained by boundary surface force, the liquid connection thereby being in direct contact with the gas bubble.

Such an electrolyte bridge represents an independent solution of the problem forming the basis of the present invention in an apparatus of the initially mentioned type. Therefore, it represents a second independent part aspect of the present invention but is, nevertheless, to be used especially advantageously in conjunction with the previously described first part aspect but, in this case, it is especially advantageous that the gas bubble is moveable through the pipe with the liquids and thus mixing of the reference electrolyte and sample liquid is continually prevented in this manner.

With the construction according to the second part aspect of the present invention, the constrasting requirements demanded of an electrolyte bridge in an electrochemical analysis apparatus are achieved in an ideal way. There are, in particular:

(a) On the one hand, the requirement that the cross-sectional area of the boundary surface between the liquid phases on both sides of the electrolyte bridge must, as mentioned, be so small that mixing up between both phases does not lead, on the one hand, to a change of the concentration of both liquids in the region of the measurement electrode, thus impairing the measurement exactitude, and, on the other hand, of the conducting-off electrode of the reference half element.

(b) On the other hand, the requirement that the necessary non-selective ion exchange between both phases must be ensured by way of the electrolyte bridge. This requirement is not only due to the fact that the total resistance of the electrochemical measurement cell, which is essentially co-determined by the resistance of the electrolyte bridge, must be considerably smaller (at least by a factor of 100) than the resistance of the measurement apparatus, but is also based upon a electrochemical reason, namely, that the exchange current density of the ions at the phase boundary surfaces must always be considerably greater than the current density caused by the measurement current. Where this condition not fulfilled, then the thermodynamic equilibrium would be disturbed to an extent impairing the measurement exactitude.

The electrolyte bridge according to the second main aspect of the present invention not only fulfils these present requirements but, in addition, avoids the initially mentioned stoppage and cleaning problems. This is especially a result of the fact that the gas bubble is in direct contact with the liquid connection overbridging it. If, in contradistinction thereto, the liquid connection were achieved in a manner in which the liquid did not have a constant contact with the gas bubble, for example, in such a manner that a capillary-shaped tubelet filled with liquid bridged over in the region of the separating air bubble, then this would automatically mean that the canal, insofar as it is sufficiently narrow in order to ensure the necessary separation of the liquids, would, on the other hand, again tend to stoppage. Thus, nothing would be achieved in comparison with the known constructions.

The liquid connection in direct contact with the gas bubble is maintained by boundary surface force. In the simplest case, this can be achieved in that the walls surrounding the gas bubble consist of the material wetted by the liquid, i.e. that the adhesion forces between the liquid particles and the wall are greater than the cohesive forces between the liquid particles themselves. This condition is fulfilled by most of the glasses and synthetic resins usual in the clinical laboratory. However, practical experiments have shown that by means of the liquid film forming in this case in the region of the gas bubble on the wall, a sufficient diffusive contact between the liquids is then only ensured when the size of the gas bubble is so percisely dimensioned that it only just fills the connecting pipe between the two liquids at the place at which the electrolyte bridge is provided. Consequently, a preferred embodiment of the present invention is especially advantageous in which the liquid of the liquid connection is in contact with solid surfaces wetted by the liquid, which surfaces are arranged so closely together that the liquid is held between them by boundary surface force. In the case of this construction, use is made of the known capillary effect, which consists in that a narrow slot fills with liquid due to the boundary surface forces becoming effective when the surfaces bounding them are wetted by the liquid and they are arranged sufficiently close to one another. The height by which the liquid ascends in a vertically arranged narrow slot against the action of gravity thereby depends, in known manner, upon the wetting properties of the surfaces and of the liquid, as well as upon the width of the slot. Since the air bubble for the purpose of the present invention is, as a rule, very small, for the purpose of the present invention, there suffices a liquid connection of at most a few millimeters in length. With the materials conventional in laboratory technology, especially synthetic resins, constructions can, without difficulty, thereby be achieved which have slots which, also in the case of a vertical arrangement of assembly, are completely filled with liquid because of the capillary effect. Some examples of such constructions are described in more detail hereinafter.

The electrolyte bridge construction according to the present invention can be achieved in a very economic manner. In cases in which a fixed-position electrolyte bridge is needed in an electrochemical measurement cell of otherwise conventional construction, at the place at which otherwise the frit or the ground glass joint would have been provided, there is provided a downwardly open housing ("pot") for the gas bubble into which opens a pipe for the introduction of the gas. The two liquids to be connected with the electrolyte bridge can then be arranged on both sides of the pot in a manner which is described hereinafter in more detail.

Insofar as the gas bubble electrolyte bridge is used in conjunction with the above-described electrolyte analyser according to the first main aspect of the present invention, it is simply achieved in that, between the reference liquid and the sample liquid, a gas bubble is sucked into the pipe which gas bubble is then, together with the two liquids, sucked through the pipe and thereby dependably prevents a rapid mixing up. The necessary liquid connection is thereby achieved by insert elements provided in the pipe, which are constructed in such a manner that the liquid is spread out by the boundary surface force between very closely neighbouring surfaces in the region of the gas bubble.

The present invention will now be described in more detail with reference to the accompanying drawings which illustrate especially preferred embodiments and in which.

Figure 5A:
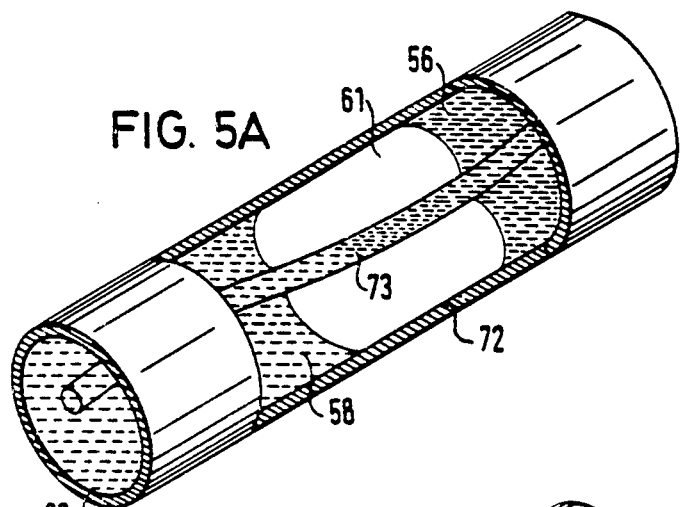
Figure 5B:
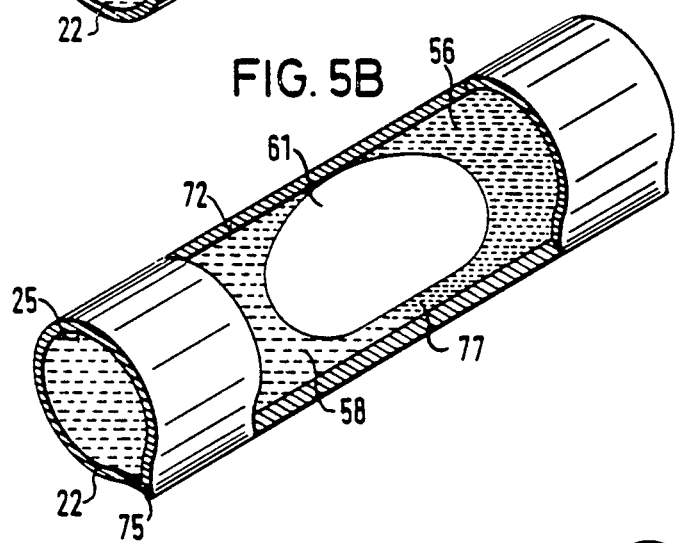
Figure 5C:
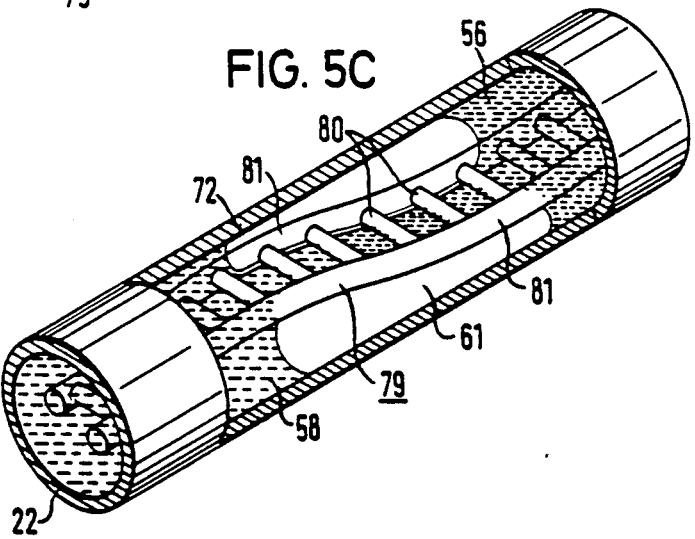
Figure 6A:
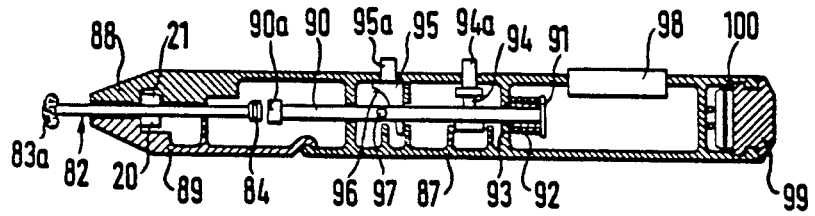
Figure 6B:
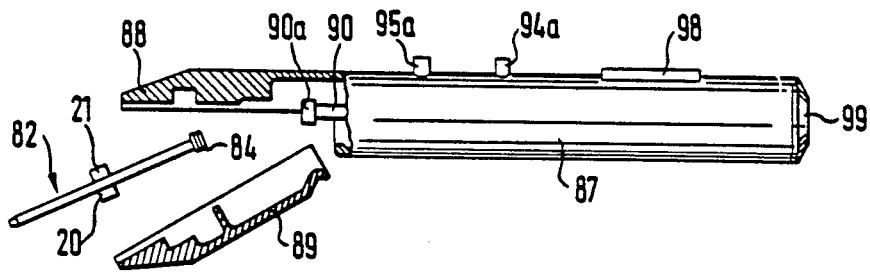
Figure 6C:
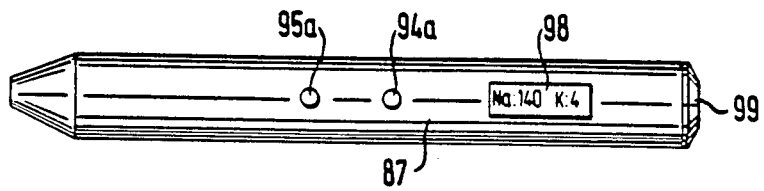
Figure 7A:
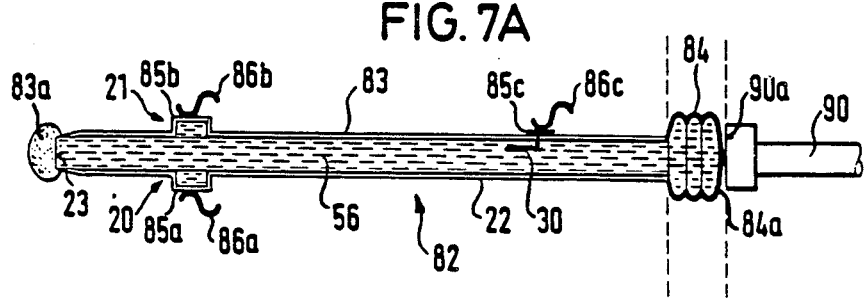
Figure 7B:
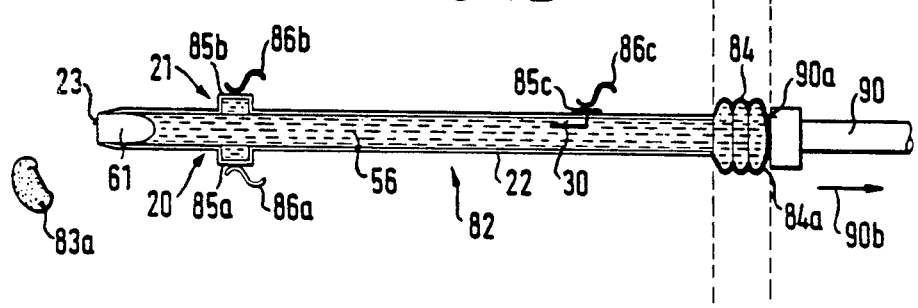
Figure 7C:
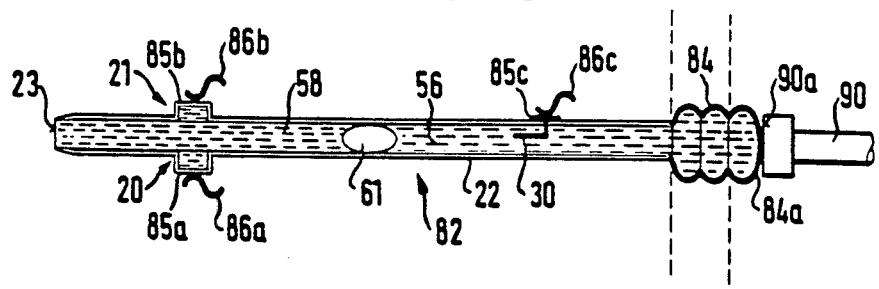
Figure 8:
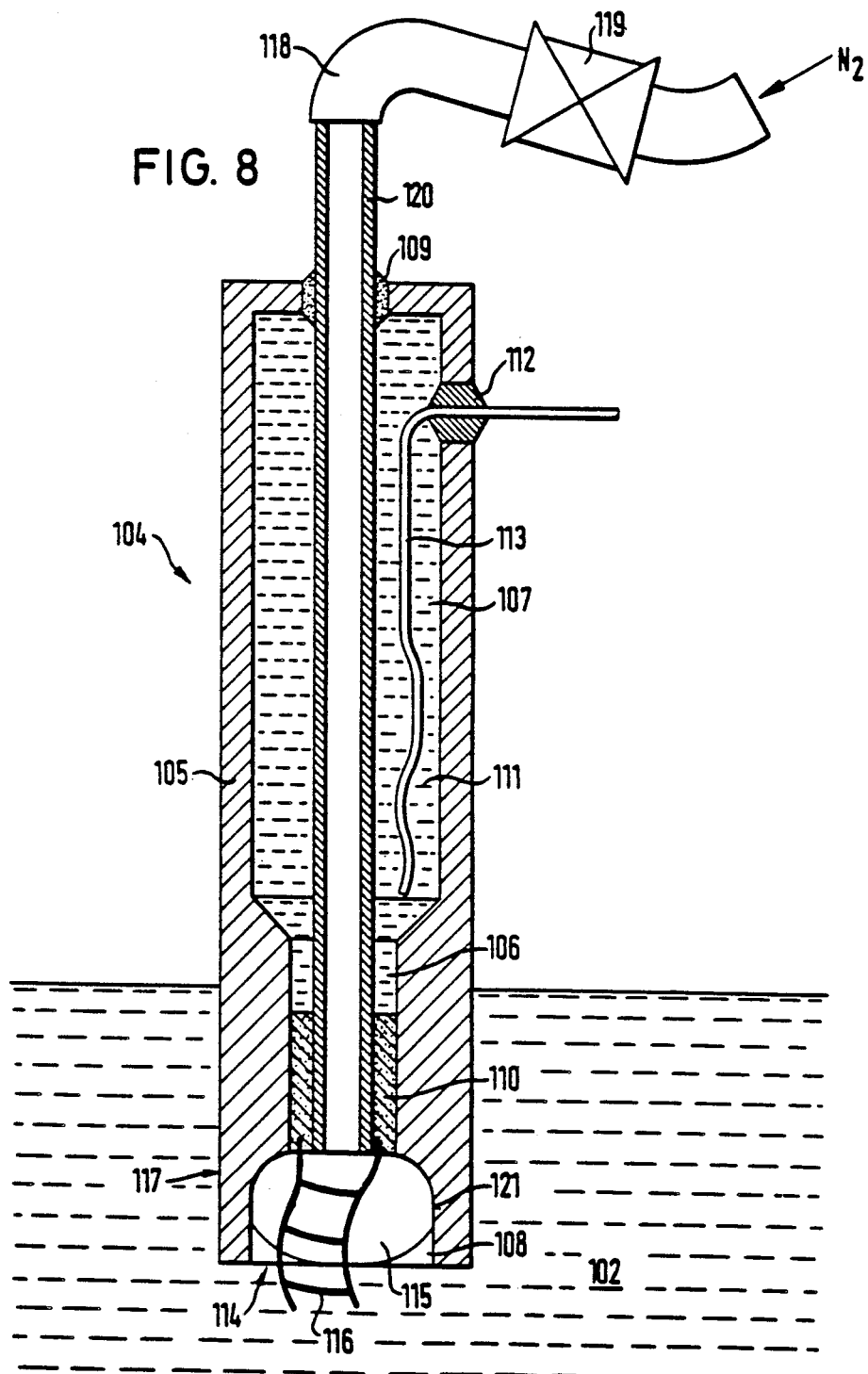

FIGS. 5(A) to 5(C) are schematic illustrations of three different embodiments of the electrolyte bridge used in conjunction with the electrolyte analyser according to the present invention;

FIGS. 6(A) to 6(C) are simplified illustrations of a preferred embodiment of an apparatus according to the present invention in which the measurement electrode, the conducting-off electrode of the reference half cell and the pipe between the sucking-in opening and conducting-off electrode are parts of an exchangeable constructional group of the electrolyte analyser, which contain the prepacked reference electrolytes;

FIGS. 7(A) to 7(C) are schematic illustrations of the exchangeable constructional group according to FIG. 6 for the explanation of the manner of functioning; and FIG. 8 is a schematic cross-sectional illustration of a reference half element according to the present invention for an otherwise conventionally constructed electrolyte analyser.

Figure 1:
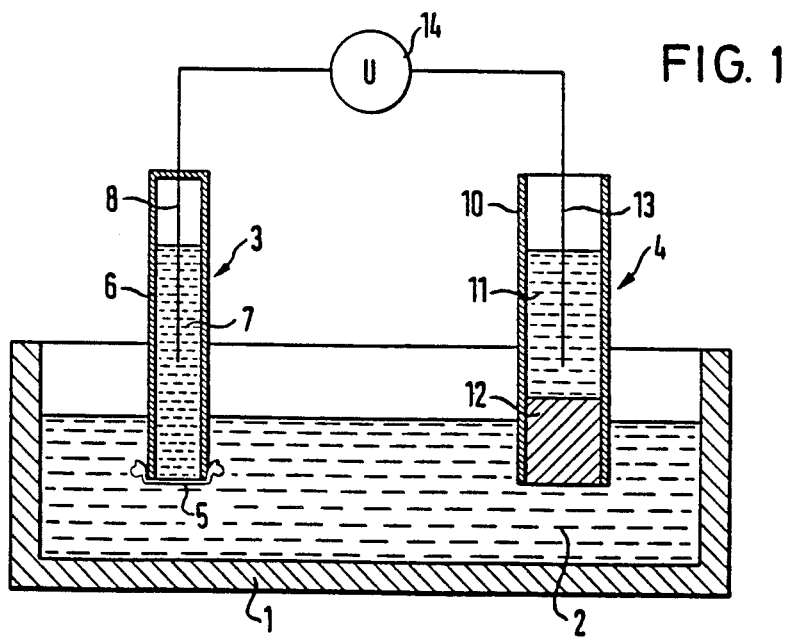
FIG. 1 is an illustration of the principle of an electrochemical measurement chain which can be used as an electrolyte analyser.

FIG. 1 shows a container 1 in which is present a sample liquid 2, an ion-selective measurement electrode 3 and a reference half element 4 dipping into the sample liquid 2.

The ion-selective electrode is constructed in known manner and includes an ion-selective membrane 5 which tightly closes off the lower opening of a corresponding housing 6. In the housing, there is present an electrolyte 7, into which projects a conducting-off element 8. Such a principle of construction of an ion-selective measurement electrode is frequently used. However, numerous other forms of construction are also well known. In principle, for the present invention there can be used the most varied types of measurement electrodes insofar as they only give a specific half cell voltage specific for the type of ion in question in contact with the measurement solution.

As is known, an ion-selective electrode alone still does not permit a measurement of activity and concentration. Only in conjunction with a reference half element 4 is it possible to measure a voltage which, according to the Nernst equation, gives conclusions regarding the activity of the ions to be detected. FIG. 1 shows the constructional principles of such as reference half element. It has a tubular housing 10 in which is present a reference electrolyte 11. Downwardly, the housing is not completely closed but rather has an electrolyte bridge 12 through which, on the one hand, the mixing of the reference electrolyte 11 with the sample liquid 2 is substantially prevented and, on the other hand, by means of which there is made possible the diffusive contact necessary for an ion conduction between the two liquids.

A conducting-off element 13 dips into the reference electrolyte liquid 11. A voltage measurement apparatus 14 is provided in order to measure the voltage between the conducting-off elements 8 and 13 and thus the measurement voltage of the electrochemical measurement chain. The voltage measurement apparatus is only illustrated schematically. As is well known, high requirements are demanded of a voltage measurement apparatus suitable for electrochemical measurement cells. In particular, it must have a very high ohmic input and be suitable for the reproducible detection of small voltages. However, such devices are known for this purpose and are commercially available so that it is not necessary to describe them here in detail.

The reference half element 4 can be constructed in many different ways. Numerous embodiments of electrolyte bridges 12 are known which, for example, are illustrated in the above-mentioned book by Cammann. It is common to these that the reference electrolyte 11 remains substantially unchanged in the housing 10 for a number of measurements and that the electrolyte bridge 12 includes one or usually a number of very small canals which are achieved by the provision of corresponding constructional parts, for example, frits, ground glass joints, wicks, ceramic materials or the like. As mentioned above, and as described in the cited article, all these embodimental forms have, however, disadvantages with regard to the simplicity of operation and of the exactitude and reproducibility over a number of measurements.

The system comprising the conducting-off element 13 and the reference electrolyte 11 can also be constructed in various ways. Thus, for example, the silver/silver chloride system is frequently employed. In this case, the reference electrolyte contains chloride ions in a definite, fixed concentration. As conducting-off element, there is used silver wire which is coated with a layer of silver chloride, an excess of solid silver chloride being present. In this way, because of the solubility product which is fixed at a given temperature, the concentration of the silver ions is coupled to the concentration of the chloride ions. On the conducting-off element 13, there takes place a reversible electrode reaction:

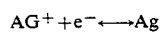

Since not only the activity of the silver but also that of the silver ions are constant, this reversible electrode reaction corresponds to a definite half cell voltage.

Another practically useful reference system is the thallium/thallous chloride system, which is constructed similarly to the silver/silver chloride system.

However, there are also considerably differing reference half cells in which other kinds of working elements are employed. To these belong reference half cells which, in turn, use ion-selective electrodes. In the case of such reference half cells, the reference electrolyte contains that type of ion for which the ion-selective electrode is selective, in fixed activity. In the case of the use of a sodium glass electrode, these are, for example, sodium ions. In some cases, known pH electrodes can also be used as conducting-off elements, the reference electrolyte thereby then having a definite H+ ion concentration, i.e. it is buffered to a definite pH value.

All these embodiments have the common feature that the conducting-off element makes, with the reference electrolyte, a reversible electrochemical reaction and the reference electrolyte contains a corresponding type of ion in a fixed concentration. There is thus obtained a constant half cell voltage which is independent of with which sample liquid 2 the reference electrolyte 11 is in contact via the electrolyte bridge 12. The measurement voltage, which the measurement apparatus 14 measures, is thus only dependent upon the half cell voltage of the measuremem electrode 3 which, in turn, is a measure of the concentration or activity of the type of ion to be analysed in the sample liquid 2.

Figure 2:
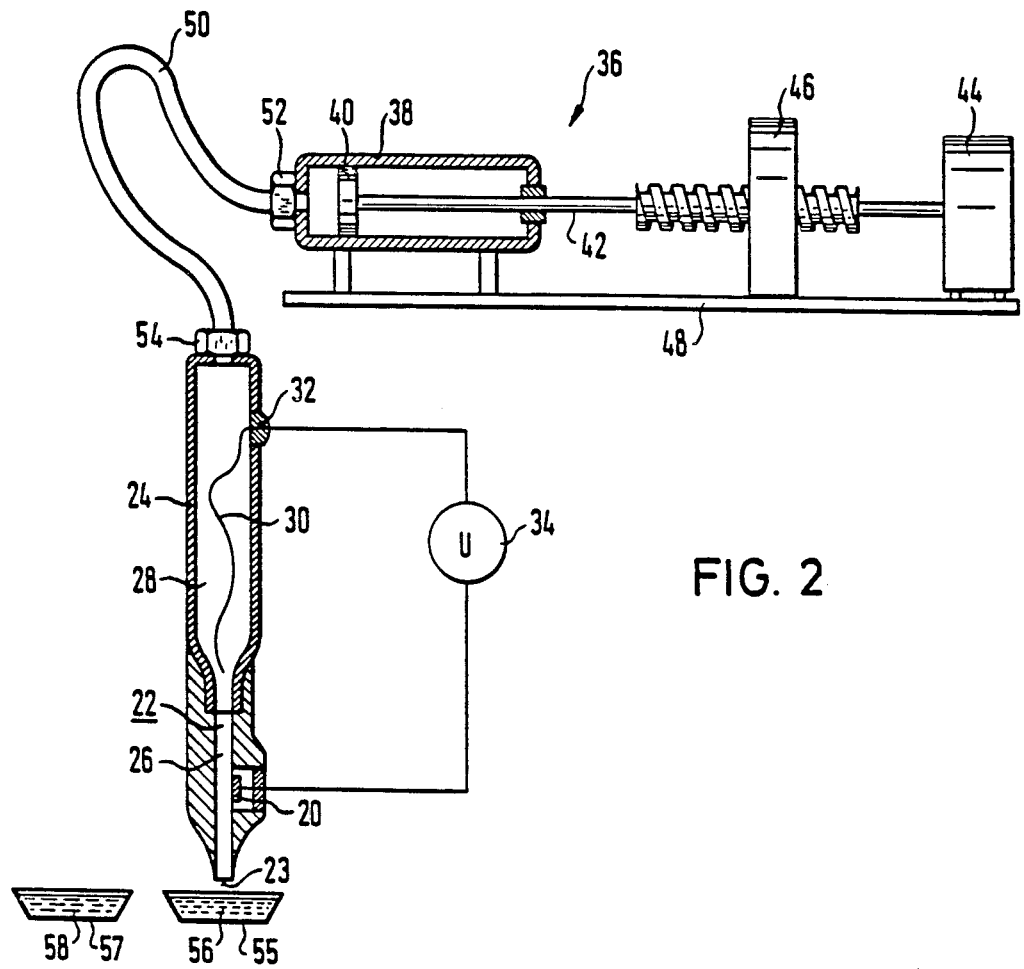
FIG. 2 is a schematic illustration of an electrolyte analyser according to the present invention, essentially in cross-section.

In Fig. 2 there is illustrated schematically and essentially in cross-section a preferred embodiment of an electrochemical electrolyte analyser according to the present invention. The measurement electrode 20 is thereby arranged on a pipe 22 which, in turn, is present in a housing 24 constructed similarly to a hand pipette such as is conventional in a clinical-chemical laboratory. The pipe 22 comprises a lower part 26, which is of tubular construction, and an upper part 28, which, in comparison with the lower part 26, is wider. On the upper part 28 of the housing 24 is provided a conducting-off element 30 of the reference half cell. In the illustrated embodiment, this is a simple wire, for example a chlorinated sivler wire, which, by means of a passage 32, is introduced in a liquid-tight manner into the upper part 28 of the pipe 22 so that it can be contacted by a liquid present in the pipe 22. The measurement electrode 20 and the conducting-off element 30 are attached to a voltage measurement device 34 which has the properties described hereinbefore.

Furthermore, a sucking-in device is provided which is indicated in its totality with the reference 36. It consists essentially of a cylinder 38 with a related piston 40, the piston rod 42 of which is connected with a drive in order to move the piston 40 back and forth in the cylinder 38. In the illustrated embodiment, the drive consists of an electromotor 44 and a worm gear 46 which, together with the piston-cylinder unit 38, 40, are mounted on a baseplate 48. Instead of the illustrated embodiment, as sucking-in device there can, for example, also be present a valve system which is connected, on the one hand, with a source of overpressure and, on the other hand, with a source of reduced pressure. The valves must, in the case of such an embodiment, be so connected for the sucking in that they connect the pipe 22 with the source of reduced pressure, whereas, for the exhaust stroke, they make a connection with the source of overpressure. Numerous other forms of a sucking-in and expulsion device are well known and can be used for the present invention. The sucking-in device 36 is connected via a pipe 50 and connection pieces 52 and 54 with the pipe 22. Below the sucking-in opening, there is a dish 55 containing the reference electrolyte liquid 56.

Furthermore, a dish 57 with sample liquid 58 is provided so that the apparatus can be put into operation.

Figure 3:
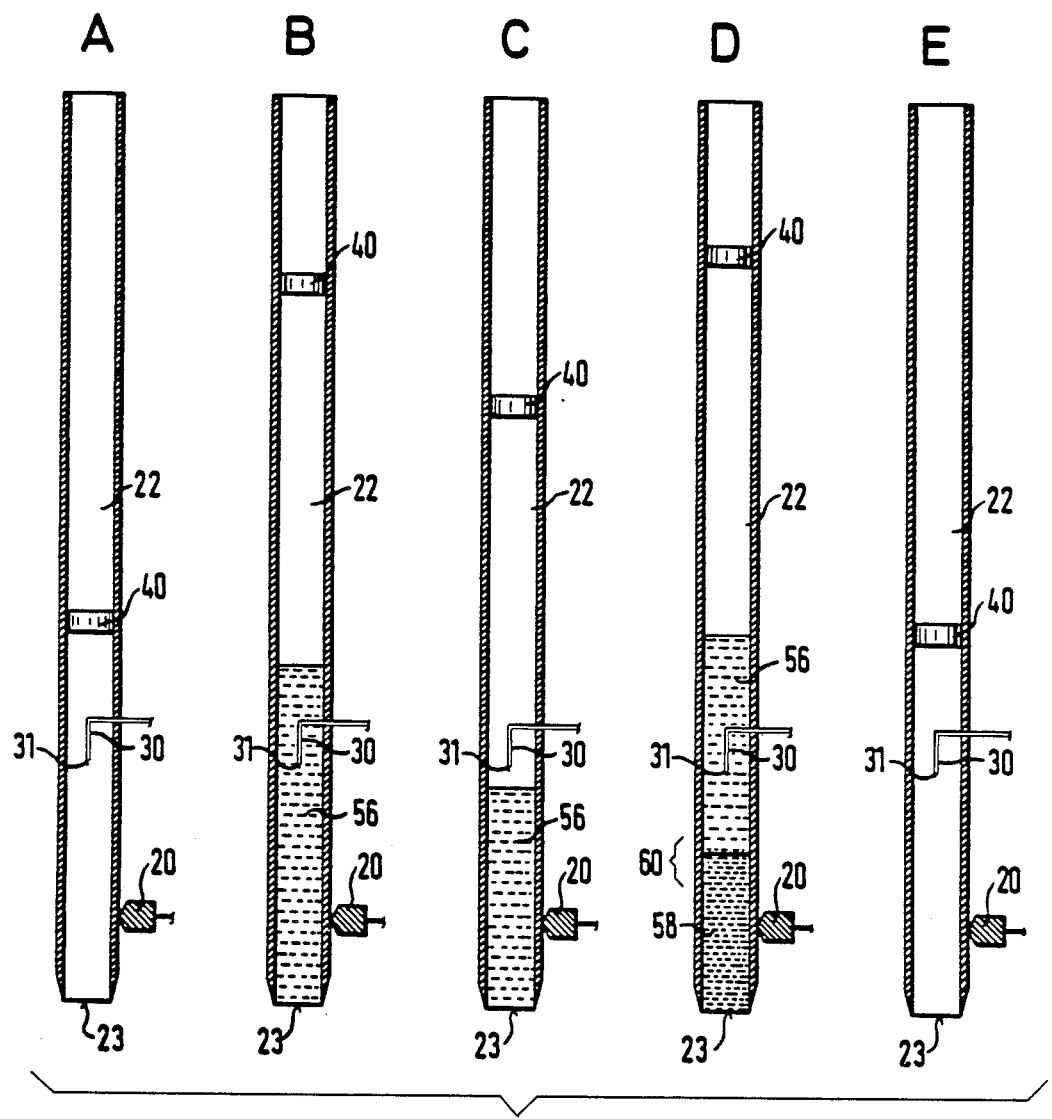
FIG. 3 is an illustration of the principle of the manner of functioning of the electrolyte analyser according to the present invention, five different operational states A to E thereby being illustrated.

The manner of functioning is explained in more detail, with reference to FIG. 3. The five different operational states A, B, C, D and E can be seen in highly schematic illustration. Corresponding parts are given the same reference numerals as in FIG. 2. There can be seen the pipe 22 with the sucking-in opening 23. Near to the sucking-in opening, the measurement electrode 20 is provided on the pipe 22, whereas the conducting-off element 30 for the reference half cell is arranged further away from the sucking-in opening 23 and thus in the sucking-in direction behind the measurement electrode 20. In the illustrated embodiment, the pipe 22 is formed with the same diameter along all of its length. In the upper part, there is present a piston 40, which serves for sucking-in and expulsion.

FIG. 3(a) shows the apparatus in the empty starting state, the piston 40 being in its lowermost position.

For the explanation of the most general manner of functioning, reference is first made to FIG. 3(C). This shows an operational state at which a definite amount of reference electrolyte liquid has been sucked in, the measurement of which will be described hereinafter. The piston 40 is present in a correspondingly higher position. The sucking-in opening 23 is now dipped into the sample liquid and the piston 40 is moved further upwards until it has reached the operational state illustrated in FIG. 3(D), which is called the measurement operational state. In this state, so much sample liquid has been sucked in directly after the reference liquid that the sample liquid contacts the measurement electrode 20, whereas the conducting-off element 30 is in contact with the reference electrolyte 56, both liquid being in contact with one another in a contact zone 60. The electrochemical measurement chain is thus closed, i.e. the voltage measurement device, which is not illustrated in this Figure, can be activated in order to measure the voltage of the measurement chain.

Of course, in the region of the contact zone, a mixing of the two liquids begins immediately, essentially by convection. Therefore, it is necessary that the sucking-in and the measurement takes place relatively quickly, namely, before, due to the mixing, the concentration in the region of the measurement electrode 20 or of the conducting-off element 30 changes and thereby falsifies the measurement.

The described sucking up procedure from the empty initial state A via the state C to the state D can take place slowly and continuously, whereby, by means of appropriate and well-known means, it must then be ensured that the voltage measurement device is activated at the right moment, i.e. when the contact zone 60 is present between the measurement electrode 20 and the conducting-off element 30. Preferably, however, the sucking-in device is operated stepwise, i.e. the piston 40 remains stationary in the illustrated positions in order, in the case of position C, to make possible the dipping into the sample liquid and, in the case of position D, the carrying out of the measurement.

After measurement has taken place, the piston 40 is moved downwardly to the position illustrated in FIG. 3(E) at which the pipe 22 is emptied and the starting position is again reached.

In the case of electrochemical measurements, usually it is not the absolute measurement value which is referred to in order to determine the concentration of the substance to be analysed but rather calibration measurements are carried out in the case of which a standard liquid is used which contains the type of ion to be determined, for example sodium or potassium, in a known concentration. In the case of the above-described manner of functioning of the device, this takes place in that, in precisely the same way as described, instead of the sample liquid 58, there is sucked up the standard liquid and, upon reaching the measurement operational state, the corresponding calibration voltage is measured.

However, an embodiment of the present invention is especially preferred in which the reference electrolyte liquid contains not only the kind of ions necessary for the function of the reference half cell, thus in the given example chloride ions, in a constant concentration but the same solution simultaneously serves as a standard and, for this purpose, also contains the kind of ions to be determined, thus for example sodium ions, in a constant and known concentration.

The manner of functioning of such an embodiment includes step B. In this case, after dipping the sucking-in opening 23 into the reference/standard solution 56, the piston is moved upwardly to the position illustrated in FIG. 3(B), i.e. to such an extent that the liquid contacts not only the measurement electrode 20 but also the conducting-off element 30. In this state, the calibration voltage can be determined very precisely since it is here a question of a measurement cell without carrying over, thus a contact zone between two different liquids with the flow possibilities resulting therefrom are present.

After the calibration measurement (calibration operational state B), the piston is again moved downwardly in order again to expel a part of the reference standard solution 56. Thereafter follows the sucking in of the sample liquid 58 and measurement of the measurement voltage in the measurement operational state D, as previously described.

The necessary amount of reference liquid which is sucked in for the achievement of operational state C or, in the case of the last described alternative, remains in the pipe 22 after the explusion, is comparatively non-critical. In principle, a very small amount would suffice which is just so great that the contact zone 60 in the measurement opertional state D is sufficiently far removed from the lower end1 of the conducting-off element 30 in order to ensure that the mixing during the measurement time does not reach up to this point. In practice, however, the amount of the reference liquid is at least about just as large as the amount of the sample liquid. Thus, an especial advantage of the device according to the present invention is the fact that the reference liquid simultaneously cleans the pipe 22 when the piston moves downwardly between states D and E and expels both liquids. For this purpose, it is preferable when the amount of reference liquid is relatively large. For this reason, also in the case of the embodiment illustrated in FIG. 2, the upper part 28 of the pipe 22 is formed with a comparatively large cross-section in order to receive considerably larger amounts of reference liquid in comparison with the amount of sample liquid.

In practical operation, it is preferable to renew the reference liquid after each measurement in order to achieve a high degree of exactitude. However, it is stressed that, in exceptional cases, another manner of operation is also possible and may be desirable in which the reference liquid remains for several measurement procedures in the pipe and is moved back and forth by the sucking-in device, whereby, in each case, only the sample liquid and a small contaminated part of the reference liquid is expelled.

Figure 4:
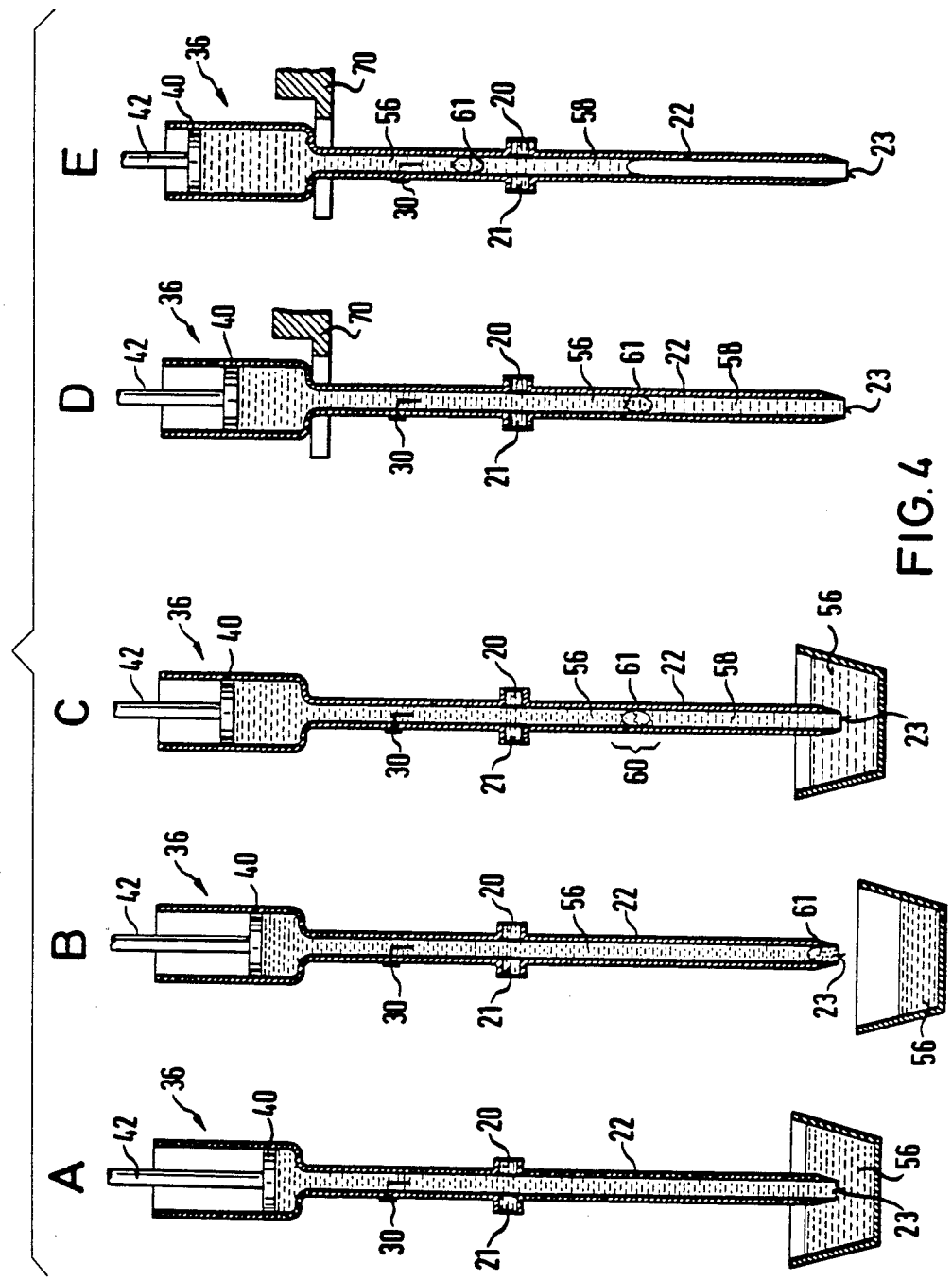
FIG. 4 is an illustration of the principle of the manner of functioning of a modified electrolyte analyser with partly automatic functions in five different operational states A to E.

FIG. 4 is an illustration similar to that of FIG. 3 but using a modified embodiment of the apparatus according to the invention, the manner of functioning of which differs in some details from that previously described. Here again, the same reference numerals are used for the corresponding parts and, in the following, there are only described the differences in comparison with the previous description.

The electrolyte analyser illustrated in FIG. 4 has two different ion-selective electrodes as measurement electrodes 20. In this way, two different kinds of ions, for example sodium and potassium, can be determined simultaneously. Of course, two standard measurements must then be carried out for the calibration, which preferably takes place in that the reference/standard solution contains both kinds of ions to be analysed in known concentrations.

The manner of functioning of the electrolyte analyser illustrated in FIG. 4 further differs in that, up to the achievement of the measurement operational state, only sucking-in procedures and no expulsion procedures are carried out. The states A, B and C are thereby achieved manually by the user, for example by means of a non-illustrated operation button, which is in connection with the piston 40 via the piston rod 42. In the manner conventional in the construction of pipettes, the apparatus can be provided with an appropriate rastering or volume adjustment means in order to simplify for the user the adjustment of the piston positions, A, B and C.

More particularly, for the achievement of the operational state A, reference/standard solution is first sucked in. Thereafter, the sucking-in opening 23 is removed from the reference electrolyte liquid 56 and the piston moved a little bit in order to suck in a small amount of air. Thereafter, the sucking-in opening 23 is dipped into the sample liquid 58 and again sucked in until a sufficient amount of sample liquid is present in the pipe 22.

By means of the sucking in of air, in the case of the embodiment illustrated in FIG. 4, use is made of the second main aspect of the present invention, namely, of an electrolyte bridge in the case of which a gas bubble arranged between the liquids is electrolytically bridged over by at least one liquid connection maintained by boundary surface force, the liquid connection thereby being in direct contact with the gas bubble. The two liquids 56 and 58 are thereby no longer in contact with one another over a large surface but rather are separated from one another by the air bubble 61. In this way, the mixing of the two liquids with one another is decisively reduced. Nevertheless, via the air bubble, an ion exchange is possible to the extent that is necessary for the functioning of the electrochemical measurement chain. Further details are described hereinafter.

After achievement of the operational state C, the electrolyte analyser is placed in an apparatus which carries out the further steps automatically and also contains the voltage measurement device.

For the sake of clarity of explanation, the drawing is highly schematic. Of the apparatus, there can only be seen the carrying arm 70 which holds the electrolyte analyser in any desired manner. At the same time, the electric contact to the ion-sensitive electrodes 20 and 21 and to the conducting-off element 30 is closed.

In order to achieve an especially high degree of exactitude, the apparatus operates in a definite time rhythm.

First, the calibration measurement is carried out in the calibration operational state illustrated in FIG. 4D. Thereafter, there is further sucking in up to state E, which corresponds to the measurement operational state. The measurement takes place at a definite, experimentally fixed point of time at which, on the one hand, a stable state has been reached and, on the other hand, no falisification of the measurement results could occur due to disturbing procedures. In the case of the sucking in from state D to state E, air is sucked into the lower part of the pipe 22 but this has no influence on the measurement result. After measurement has taken place, the whole liquid is expelled, as previously described.

The use of a gas bubble and especially of an air bubble for the separation of the two liquids offers, as can readily be appreciated, considerable advantages because the reference electrolyte and the measurement liquid can only mix relatively slowly. In this way, the precision of the measurement is decisively improved. It is to be stressed that the air bubble separates both liquids during the whole sucking in and expulsion procedure, whereas a corresponding construction of the pipe, for example, a constriction preventing the liquid exchange in the region in which the contact zone 60 between the two liquids is present in the measurement operational state, would only permit the achievement of the desired separation action during this state.

In order, in spite of the separation by the air bubble, to maintain an electrolyte bridge between the two liquids, as is necessary for the functioning of the electrochemical measurement chain, boundary surface forces are utilised. In the region of the pipe 22 in which is present the contact zone 60 in the measurement operational state, for this purpose surfaces must be present which have the property of being wetted by the liquids.

In the simplest case, a thin film of liquid on the wall, which is maintained by the boundary surface forces, forms the necessary liquid bridge. However, practical experiments have shown that only in a very narrow range of the air bubble size is this, on the one hand, so great that it can be sucked in reproducibly and certainly and, on the other hand, is sufficiently small that the liquid film forms a sufficient electrolyte bridge on the wall. Since, in practice, this is very difficult to realise dependably, additional measures are preferably resorted to which, in total, are characterised in that the liquid of the liquid connection is in contact with solid surfaces moistened by the liquid which are arranged so closely to one another that the liquid is held between them by boundary surface force.

One of the surfaces arranged closely together and necessary for this purpose can be formed by the inner wall of the housing surrounding the gas bubble, thus in the illustrated embodiment by the inner wall of the pipe 22, which is indicated in FIG. 5 by reference 72.

FIG. 5A shows, in a schematic, partially cut away perspective view, a section of the pipe 22 in which the gas bubble 61 can be seen, which separates the liquids 56 and 58. For the maintenance of the electrolytic connection, as insert there is introduced a thin filament 73 which consists of a material wetted by the liquid. Between the inner wall 72 and the surface of the filament 73 facing it there lies, in the case of this embodiment, a narrow slot which, because of the described capillary effect, is filled with liquid. In a practically useful embodiment, in a pipe with an inner diameter of 0.75 mm. there was placed a nylon thread of about 0.26 mm. diameter. In the case of an air bubble volume of 5 $\mu$l., there was thereby given, without the thread, an electrical resistance over the contact zone of 17.0M $\mu$, a value which is so high that a precise measurement of the electrochemical measurement chain voltage is made very difficult. After introduction of the nylon thread, there was obtained a resistance of 250K $\Omega$, which readily permits an exact electrochemical measurement. (The resistance of the corresponding measurement length without the air bubble was 100K $\Omega$).

Another method of lowering the electrolytic resistance in the case of using a separating air bubble is illustrated in FIG. 5B. It can be seen that the pipe 22 has, in this case, an asymmetrical cross-section which, at one point of its circumference, is pointed. In this way, on the inner wall 72 of the pipe 22 there is a sharp angle 75 running its length. In the region of this sharp angle, the surfaces of the inner wall 72 are so close to one another that a capillary effect arises, i.e. the region between the surfaces bounding the angle are completely filled, as is indicated in the drawing by reference 77. In this case, the wall surrounding the air bubble is so constructed that both surfaces necessary for the formation of the liquid connection are formed by it. This can, for example, also be achieved by a corresponding longitudinal groove in the inner wall 72 of the pipe 22. A practical experiment was carried out using a tube of polyvinyl chloride (trade mark "Tygon") which had an inner diameter of 2.5 mm. and which had been asymmetrically squeezed out in a form corresponding to FIG. 5B. During the slow squeezing together over a 3.8 cm. long piece of tube, a sudden change of resistance took place, a resistance value of about 75K $\Omega$ thereby readily being obtained without the separating air bubble being impaired.

The embodiment illustrated in FIG. 5C is an example of a construction in which an insert part is used which extends over the gas bubble and itself, thus without the help of the inner wall of the pipe, has surfaces which are arranged sufficiently close together in order to achieve the described capillary effect. For this purpose, there are especially suitable all constructions in which the longitudinal threads are kept at a distance apart by appropriate transverse structures. This can already be achieved by an appropriate entwining of the longitudinal threads but here, however, contamination problems could again arise. Therefore, a more appropriate construction is one in which the individual threads are kept a distance apart by transverse members. FIG. 5C shows a ladder-like insert member 79 which, for example, can be made of polyamide. The transverse pieces 80 and/or the longitudinal threads 81 can thereby be arranged so close to one another that surfaces lying opposite one another only leave a slot therebetween which, because of the boundary surface forces, is completely filled by the liquid in the form of a capillary effect.

A number of other constructions for an appropriate liquid connection can also be provided. For example, the inner wall 25 of the pipe 22 can have longitudinal canals which fill up by means of a capillary effect. It is important, in connection with the present invention, that the liquid forming the liquid connection is in direct contact with the gas bubble. If, in contradistinction thereto, a parallel canal were, for example, provided which, in a special capillary-shaped pipe, passed by the air bubble in order to achieve the necessary electrolyte bridge, then here too an electrolyte connection would be achieved but the conduction present in this capillary would remain in the capillary during the expulsion of the liquid and, in the case of comparatively long operation, would lead to contamination.

Quite especial practical handling advantages are possessed by an embodiment of the apparatus according to the present invention such as are illustrated in FIGS. 6 and 7. In the case of this embodiment, the measurement electrodes 20, 21, the conducting-off electrodes of the reference half cell 30 and the pipe 22 between the sucking-in opening 23 and the conducting-off electrode 30 are parts of an exchangeable constructional set which is indicated by reference 82. FIG. 6 shows this constructional set incorporated into an appropriate apparatus and FIG. 7 shows, in the three phases A, B and C, the manner of functioning of this preferred embodiment.

In FIG. 7A, there can be seen this exchangeable constructional set which, in the following, for the sake of simplicity, is called a disposable measurement cell, in the state in which it is provided by the manufacturer for use in the apparatus. It consists essentially of a synthetic resin housing 83, the middle tube-shaped part of which forms the pipe 22. On the left-hand side end of the pipe 22 shown in the drawing, there is provided the sucking-in opening 23. In the case of the disposable measurement cell, it is closed by a synthetic resin part 83a which is securely attached, being preferably cast on in one piece, and separable at a marked breaking-off point, this part 83a hereinafter being called a closure cap. On the end remote from sucking-in opening 23, the synthetic resin housing 83 is formed into an elastic bellows 84. The synthetic resin housing 83 is already completely filled with a reference/standard solution by the manufacturer of the disposable measurement cell, which solution contains, in the previously described manner, not only one or more sought after kinds of ions in known concentration but also a constant concentration of the electrolytes necessary for the reference half cell. For the measurement, the disposable measurement cell 82 has two different measurement electrodes 20 and 21, for example for sodium and potassium, as well as the conducting-off element 30 of the reference half cell. The electrodes and the conducting-off element are outwardly connected with contact surfaces 85a, 85b and 85c against which, in an assembled state, there lie sliders 86a, 86b and 86c which provide the connection to the actual apparatus.

The incorporation of the disposable measurement cell 82 into the apparatus can be seen from FIG. 6. The apparatus housing 87 is, for reasons of simplicity of handling, formed in the illustrated embodiment similar to a hand pipette conventional in a clinical laboratory. On the left end thereof in the Figure, there is the measurement cell receiver 88 into which, in the initial state illustrated in FIG. 6A), there is inserted a disposable measurement cell 82. The measurement cell receiver is closed with a cover 89. It is constructed in such a manner that, possibly in cooperation with the cover 89, the disposable measurement cell 82 is fixedly positioned after insertion in the apparatus.

In the centre of the apparatus, there can be seen a striker member 90 which has a stop surface 90a which faces the bellows 84 of the disposable measurement cell 82. The striker member 90 has, on its end remote from the stop surface 90a, a spring flange 91 against which a pressure spring 92 presses, which abuts with its other end on an appropriate projection 93 of the housing 87. The striker member is firmly held in the position illustrated in FIG. 6A by means of a holding element 94 which can be operated with a button 94a. Details of a construction appropriate for this purpose are well known and are not illustrated in detail in the drawing. Upon pressing the button 94a, the holding of the striker member 90 is freed so that, by the action of the spring, it can move from left to right in the embodiment as illustrated in the Figure. With a further button 95a, a return element 95 can be operated, by means of which the striker member is again returned to the starting position illustrated in FIG. 6A. In the Figure, there can be seen a curved surface 96 on the return element and a pin 97 arranged transversely to the direction of movement, by the working together of which the restoration is achieved in known manner. Finally, from the Figure there is to be seen the arrangement of a measurement and indicator unit 98 and of a battery 100 positioned under a cover 99.

From FIG. 7, it can be seen how this preferred construction is used. FIG. 7A shows, as described, the initial position after insertion into the apparatus. Between the rear end 84a and the stop surface 90a of the striker member 90, there is present a narrow slit. If the closure cap 83a is now twisted off from the synthetic resin housing 83, then the bellows 84 expands because of its inherent tension until its surface 84a lies against the surface 90a. In this way, an air bubble 61 is sucked into the front end of the disposable measurement cell 82, as is illustrated in FIG. 7B. The reference/standard solution thereby contacts, at the front as well as behind, not only the measurement electrodes 20 and 21 but also the conducting-off element of the reference half cell. The calibration measurement can be carried out not only in the operational state illustrated in FIG. 7A but also in that illustrated in FIG. 7B.

The sucking-in opening 23 is now dipped into a sample liquid and the button 94a of the holding element 94 is operated so that the striker member 90, as described and as indicated by the arrow 90b in FIG. 7B, moves away from the bellows 84. The bellows 84 can thereby again relax and sample liquid is sucked into the sucking-in opening 23 until it has reached the position illustrated in FIG. 7C, at which the bellows 84 again lies against the stop surface 90a of the striker member 90. The contact zone between the reference/standard solution 56 and the sample liquid 58 with the air bubble 61 is now found to be between the measurement electrodes 20, 21 and the conducting-off element 30 of the reference half cell. The measurement operational state is thereby achieved and the voltage measurement device can be activated in order to determine the characteristic measurement voltage in the sample liquid for the sought concentration of the kind of ion to be determined.

By operation of the button 95a, the striker member 90 is moved back into the initial position via the return element 95. With the help of a simple mechanism, which, for the sake of clarity is not illustrated in FIG. 6, the stopping of the cover 89 is thereby released so that this opens and the disposable measurement cell 82 drops out, as is illustrated in FIG. 6B.

FIG. 6C shows the corresponding apparatus in a position rotated 90° about its longitudinal axis in order that there can be seen the outer construction and the arrangement of the operating buttons 94a and 95a, as well as the indicator 98.

FIG. 8 shows, essentially in cross-section, a reference half element which has an electrolyte bridge according to the second main feature of the present invention. However, the gas bubble is here not, as in the case described in FIGS. 2 to 6, in a pipe in which the reference liquid and the sample liquid flow, separated by the gas bubble, but rather is present in a stationary reference half element which can be used in combination with a conventional electrolyte analyser, such as is illustrated in FIG. 1, instead of the reference half element 4.

The reference half element 104 illustrated in FIG. 8 has a housing 105 with an inner bore which has a comparatively narrow middle region 106, a widened upper region 107 and a widened lower region 108.

Centrally, in the middle and upper region 106, 107, there is provided a gas pipe 120 which is fixed in a liquid-tight manner with an adhesive seal 109 on to the housing 105. On the lower end of the gas pipe 120, there is present, between its outer wall and the inner wall of the middle region 106, a stuffed wick 110 or a similar porous body. Its porosity must be such that the reference electrolyte 111 present above it essentially in the upper region 107 of the inner bore of the housing 105 cannot run out downwardly. Into the electrolyte, there extends, through a liquid-tight passage 112, a conducting-off element 113, for example a chloridised silver wire in the case of an Ag/AgCl reference half element.

The lower widened region 108 of the inner bore of the housing 105 forms a pot-like, downwardly open housing 114 for the air bubble 115. The reference half element 104 is dipped into a sample liquid 102 corresponding to the half element 4 into the liquid 2 in FIG. 1. The essential difference to the there-illustrated construction is that the electrolyte bridge making possible a diffusive exchange of the ions and, at the same time, substantially preventing a mixing is here not realised with the help of a frit, a ground glass joint or like construction but rather with the air bubble 115 which is bridged over by a ladder-like insert part 116 which corresponds essentially to the insert part described in connection with FIG. 5C. The gas bubble is produced by blowing in gas, for example air or possibly nitrogen, through the pipe 118 into the gas pipe 120 and remains, after closure of the valve 119, in the pot-shaped housing 114.

Such a reference half element with a gas bubble can scarcely become blocked. It is thereby to be observed that the stuffed wick 110 does not come into direct contact with the sample liquid 102 and, consequently, shows a substantially lesser tendency to stoppage than the narrow canals of the previously known electrolyte bridges. It is thereby also important that its capillaries can be relatively narrow. It must not be so compact that the reference electrolyte liquid 111 remains in the housing 105, which is relatively simple to bring about since the housing is closed on all sides.

The gas bubble is, in the case of this illustrated embodiment, alterable during operation, even in its size, by the introduction or release of gas. By blowing in additional gas, it can be made so large that there is achieved a practically complete separation between the two liquids when the apparatus is not used for a comparatively long period of time. For operation, some gas is then released until a sufficient conductivity via the electrolyte bridge is reached. Instead of the ladder-like insert part 116, there can thereby, of course, also be used one of the other previously described constructions, the inner wall 121 of the pot-like housing 114 there preferably being made of a wettable material.

It will be understood that the specification and examples are illustrative but not limitative of the present invention and that other embodiments within the spirit and scope of the invention will suggest themselves to those skilled in the art.

We claim:

1. A method of making an electrochemical analysis of electrolytic components in a sample liquid, especially of a body fluid, utilizing a device comprising a selective measurement electrode for a kind of ion to be analyzed, a reference half-cell which includes a conducting-off element co-operating in the operational state with a reference electrolyte, a voltage measurement device for the measurement of the voltage between the measurement electrode and the conducting-off element, a pipe provided with a sucking-in opening for the sample liquid and having the measurement electrode disposed thereon, the conducting-off element of the reference half-cell being arranged on the pipe in the sucking-in direction behind the measurement electrode in such a manner that it directly contacts a liquid reference electrolyte present in the pipe which liquid contains a species of ions in fixed concentration which makes a reversible electrochemical reaction with the conducting-off element, comprising:

sucking-in into the pipe a sample liquid and transporting the sample liquid, together with the liquid reference electrolyte present in the pipe, with respect to the pipe in the same direction as the sucking-in direction in the pipe for causing the sample liquid to contact the measurement electrode and for causing the reference electrolyte to contact the conducting-off element simultaneously while both liquids are in contact with each other, activating the voltage measurement device in a measurement operational state in that the sample liquid contacts the measurement electrode and the reference electrolyte contacts the conducting-off element and both liquids are in contact with one another.

2. A method according to claim 1, comprising:

sucking-in into the pipe after the liquid reference electrolyte present in the pipe, a gas bubble; and, sucking-in into the pipe the sample liquid after the gas bubble and transporting the sample liquid, together with the liquid reference electrolyte and the gas bubble present in the pipe, the gas bubble, positioned between the liquids, forming in the measurement operational state an electrolyte bridge, which bubble is electrolytically bridged over by at least one liquid connection maintained by boundary surface force, the liquid connection thereby being in direct contact with the gas bubble.

3. A method according to claim 2, wherein the liquid of the liquid connection is in contact with solid surfaces wetted by the liquid, which surfaces are arranged closely together so that the liquid is held between them by boundary surface force.

4. A method according to claim 3, wherein the surfaces belong to an insert part which extends over the gas bubble and has constructional parts arranged sufficiently close together.

5. A method according to claim 3, wherein at least one of the surfaces is formed by a wall surrounding the air bubble.

6. A method according to claim 5, wherein an insert part is provided, the surface of which cooperates with the surface of said wall in order to hold the liquid by boundary surface force.

7. A method according to claim 2, wherein the gas bubble is alterable in its size by the introduction or removal of gas.

8. A method according to claim 1, wherein the reference electrolyte additionally to the species of ions which makes a reversible electrochemical reaction with the conducting-off element contains the species of ions to be determined in known activity so that it forms a combined reference/standard solution and the voltage measurement device is activated in a calibration operational state in that the combined reference/standard solution contacts the measurement electrode and the conducting-off element in order to obtain a calibration measurement value.

9. A method according to claim 1, wherein the sucking-in of the sample liquid is stopped when a definite volume is sucked in and said definite volume for the sample liquid and the volume of the pipe are coordinated with one another in such a manner that, when the sucking in of the sample liquid is stopped in the measurement operational state, a contact zone between the reference electrolyte and the sample liquid is present in the pipe region between the measurement electrode and the conducting-off element.

10. A method according to claim 1, wherein the pipe, in the region in which the contact zone between the reference liquid and the sample liquid is present in the measurement operational state, has an electrolyte bridge which prevents a mixing up between the reference electrolytes and sample liquid.

* * * * *

UNITED STATES PATENT AND TRADEMARK OFFICE
CERTIFICATE OF CORRECTION

PATENT NO. : 4,838,999
DATED : June 13, 1989
INVENTOR(S) : Hans-Peter Haar, et al.

It is certified that error appears in the above-identified patent and that said Letters Patent is hereby corrected as shown below:

Column 2 line 5 for "eledtrodes" read -- electrodes --.

Column 2 line 44 for "samll" read -- small --.

Column 4, line 35 for "The" read -- In --.

Column 11, line 44 for "endl" read -- end 31 --.

Column 14, line 2 for "17.0M$\mu$ " read -- 17.0M $\Omega$ --.

Signed and Sealed this

Twenty-eighth Day of July, 1992

Attest:

DOUGLAS B. COMER

Attesting Officer    Acting Commissioner of Patents and Trademarks